US008860447B2

(12) United States Patent
Vedagarbha et al.

(10) Patent No.: US 8,860,447 B2
(45) Date of Patent: Oct. 14, 2014

(54) LASER ASSISTED DEVICE ALTERATION USING TWO-PHOTON ABSORPTION

(75) Inventors: Praveen Vedagarbha, Fremont, CA (US); Derryck Reid, Blackridge (GB)

(73) Assignee: DCG Systems, Inc., Fremont, CA (US)

( * ) Notice: Subject to any disclaimer, the term of this patent is extended or adjusted under 35 U.S.C. 154(b) by 429 days.

(21) Appl. No.: 13/228,369

(22) Filed: Sep. 8, 2011

(65) Prior Publication Data

US 2012/0056626 A1 Mar. 8, 2012

Related U.S. Application Data

(60) Provisional application No. 61/381,023, filed on Sep. 8, 2010.

(51) Int. Cl.
*G01R 31/311* (2006.01)
*G01R 31/303* (2006.01)

(52) U.S. Cl.
CPC ............ *G01R 31/311* (2013.01); *G01R 31/303* (2013.01)
USPC ................................. 324/754.06; 324/758.02

(58) Field of Classification Search
CPC ........................... G01R 31/311; G01R 31/303
USPC ........................................ 324/754.06, 758.02
See application file for complete search history.

(56) References Cited

U.S. PATENT DOCUMENTS

| | | | |
|---|---|---|---|
| 5,095,262 A | 3/1992 | Henley et al. | |
| 5,546,011 A * | 8/1996 | Takahashi et al. | ....... 324/754.03 |
| 6,316,950 B1 * | 11/2001 | Denk et al. | ............... 324/754.23 |
| 6,400,165 B1 * | 6/2002 | Knox et al. | .............. 324/754.06 |
| 6,882,170 B2 * | 4/2005 | Eiles et al. | ............... 324/750.03 |
| 7,516,379 B2 * | 4/2009 | Rohrbaugh et al. | .......... 714/731 |
| 2007/0002328 A1 | 1/2007 | Woods et al. | |
| 2009/0213879 A1 | 8/2009 | Stadler et al. | |
| 2012/0056626 A1 | 3/2012 | Vedagarbha et al. | |
| 2013/0314116 A1 | 11/2013 | Vedagarbha et al. | |

FOREIGN PATENT DOCUMENTS

| | | |
|---|---|---|
| CN | 1592854 A | 3/2005 |
| CN | 102401632 A | 4/2012 |
| EP | 2428807 A2 | 3/2012 |
| JP | 2012-058247 A | 3/2012 |
| TW | 200937504 A | 9/2009 |
| TW | 200944821 A | 11/2009 |
| WO | 2013/188046 A1 | 12/2013 |

OTHER PUBLICATIONS

Rostami et al. "A Proposal for Fast Optical Switch using Two-photon Absorption Coupled Ring-resonator to MZI". Published in 2005 for IEEE. pp. 66-69.*

(Continued)

*Primary Examiner* — Jeff Natalini
(74) *Attorney, Agent, or Firm* — Nixon Peabody LLP; Joseph Bach, Esq.

(57) ABSTRACT

A Two-Photon Laser Assisted Device Alteration technique is presented. Fault localization is investigated by exploiting the non-linear two-photon absorption mechanism to induce LADA effects. Femtosecond laser pulses of wavelength having photon energy lower than the silicon bandgap are directed at the area of interest, while the DUT is stimulated with test vectors. The laser pulses are synchronized to the DUT stimulation, so that switching timing can be altered using the two-photon absorption effect.

12 Claims, 1 Drawing Sheet

(56) References Cited

OTHER PUBLICATIONS

Niu, B. et al., "Two-Photon Absorption Laser Assisted Device Alteration Using 1340nm CW Laser: Critical Timing Fault Isolation & Localization for 32nm MPU and Beyond," ASM International, Proceedings from the 36th International Symposium for Testing and Failure Analysis, Nov. 14-18, 2010, pp. 224-230.

Bautista, G. S., Jr. et al., "Two-Photon Optical Beam-Induced Current Microscopy of Light-Emitting Diodes," Science Diliman, Jul.-Dec. 2004, 16:2, pp. 61-65.

Serrels, K. A. et al., "Two-Photon X-Variation Mapping Based on a Diode-Pumped Femtosecond Laser," ASM International, Proceedings from the 36th International Symposium for Testing and Failure Analysis, Nov. 14-18, 2010, pp. 14-19.

Pouget, V. et al., "Picosecond Single-Photon and Femtosecond Two-Photon Pulsed Laser Stimulation for IC Characterization and Failure Analysis," ASM International, Conference Proceedings from the 35th International Symposium for Testing and Failure Analysis, Nov. 15-19, 2009, pp. 268-271.

Serrels, K. A. et al., "Two-Photon X-Variation Mapping Based on a Diode-Pumped Femtosecond Laser," DCG Systems Presentation, Emerging FA Technologies & Concepts, ISTFA 2010, Nov. 16-18, 2010, 19 pages.

International Search Report and Written Opinion for PCT/US2013/041468 dated Nov. 14, 2013.

Examination Report for Taiwanese Patent Application No. 100132283 dated Oct. 21, 2013.

Examination Report for Taiwanese Patent Application No. 102117339 dated Aug. 29, 2014. (Matter 127073).

* cited by examiner

LASER ASSISTED DEVICE ALTERATION USING TWO-PHOTON ABSORPTION

RELATED APPLICATION

This Application claims priority benefit from U.S. Provisional Patent Application No. 61/381,023, filed Sep. 8, 2010, the disclosure of which is incorporated herein by reference in its entirety.

BACKGROUND

1. Field of the Application

This invention is in the field of laser based defect localization analysis of integrated circuits, and, more specifically, in the field of design debug and/or failure analysis of integrated circuits using laser illumination.

2. Related Art

Laser Assisted Device Alteration (LADA) is a technique employed in the test and debug stage of chip design. It is specifically used for isolating critical performance limiting nodes in complex, defect-free integrated circuits. It has also found wide use in localizing process defects as the LADA effect easily modulates transistor characteristics in the same path as the process defect.

The LADA technique is based on the ability of a continuous wave (CW) laser to generate localized photocurrents in an integrated circuit's backside, and thus change the pass/fail outcome of a test stimulus on a "sensitive" transistor and identify the location of faults. The laser is typically of a short wavelength variety on the order of 1064 nm, so that the photon energy is above the silicon indirect band gap (about 1107 nm). This photon energy is required in order to initiate the single photon effect that is used to change the transistor's behavior. Due to the limitation on selection of wavelength of the laser, the current spatial resolution of the localized fault is about 240 nm.

FIG. 1 illustrates a conventional LADA system, which uses a continuous wave laser to induce single-photon electron-hole pairs in the device under test (DUT) from the backside of the chip. A DUT 110 is coupled to a tester 115, e.g., a conventional Automated Testing Equipment (ATE), which is connected to computer 150. The ATE is used in a conventional manner to stimulate the DUT with test vectors and study the response of the DUT to the test vectors. The response of the DUT to the test vectors can be further investigated using the LADA. For example, if the DUT fails a certain test, LADA can be used to investigate whether the DUT can pass under certain conditions and, if so, which device, i.e., transistor, was responsible for the failure. Conversely, when the DUT passes certain tests, LADA can be used to investigate under which conditions the DUT will fail these tests and, if so, which device, i.e., transistor, was responsible for the failure.

The LADA system operates as follows. Tiltable mirrors 130 and 135 and objective lens 140 are used to focus and scan a beam from CW laser 120 onto the DUT 110. This allows the laser 120 to generate photo carriers in the silicon of the DUT without resulting in localized heating of the device. The electron-hole pairs so generated affect the timing of the nearby transistor, i.e., decreasing or increasing transistor switching time. The tester is configured to place the operating point of the device under test in a marginal state by applying a recurrent test loop of selected voltage and frequency. The laser stimulation is then used to change the outcome of the tester's pass/fail status. The beam's location at each point is correlated to the pass/fail outcome of the tester, so that when a change is detected, i.e., a previously passing transistor is now failing or vice versa, the coordinates of the laser beam at that time points to the location of the "borderline" transistor.

The present state-of-the-art in laser assisted fault localization is of about 240 nm resolution. The limitation on further improvement of the single photon LADA resolution is imposed by the laser light wavelength. Optical absorption of silicon at smaller than 1064 nm becomes the major obstacle for delivering light to the transistor through the backside. However due to the continued scaling of chip designs, higher resolution is required in order to provide fault localization in state of the art chips. For example, at 22 nm design rule it is doubtful that conventional LADA will be able to resolve among four neighboring transistors.

Optical beam induced current (OBIC) is another test and debug analysis in which laser beam is illuminating the DUT. However, unlike LADA, OBIC is a static test, meaning no stimulus signal is applied to the DUT. Instead, the laser beam is used to induce current in the DUT, which is then measured using low-noise, high-gain voltage or current amplifiers. OBIC has been used in a single-photon mode and in a two-photon absorption mode, sometimes referred to as TOBIC or 2P-OBIC (two-photon optical beam induced current).

Two-photon absorption (TPA) is the simultaneous absorption of two photons of identical or different frequencies in order to excite a molecule from one state (usually the ground state) to a higher energy electronic state. The wavelength is chosen such that the sum of the photon energy of two photons arriving at the same time is equal to the energy difference between the involved lower and upper states of the molecule. Two-photon absorption is a second-order process, several orders of magnitude weaker than linear (single-photon) absorption. It differs from linear absorption in that the strength of absorption depends on the square of the light intensity, thus it is a nonlinear optical process.

FIG. 3 illustrates a comparison of a single-photon absorption on the left and two-photon absorption on the right. Since the absorption of two-photon is a second order process, it enables a 1.4 (2) times higher resolution than single-photon absorption. However, it requires a higher peak power, pulsed beam, so that the probability of two photons arriving at exactly the same time is drastically increased. Therefore, femtosecond laser pulses, with pulse width of about 100 fs, have been used in the art to generate two-photon absorption.

SUMMARY

The following summary of the disclosure is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Embodiments of the invention enable higher resolution of fault localization by exploiting the non-linear two-photon absorption mechanism to induce LADA effects. This technique is referred to herein as Two-Photon Laser Assisted Device Alteration technique.

Embodiments of the invention enable higher resolution of fault localization by using test vectors stimulating a DUT and at the same time use a femtosecond pulsed laser to scan an area of interest in the DUT and examine the response of the DUT to the test vectors during the scan. The laser source is chosen such that the wavelength provides photon energy below the band gap of silicon and it provides pulses of femtosecond pulse width.

BRIEF DESCRIPTION OF THE DRAWINGS

Other aspects and features of the invention would be apparent from the detailed description, which is made with reference to the following drawings. It should be appreciated that the detailed description and the drawings provides various non-limiting examples of various embodiments of the invention, which is defined by the appended claims.

DETAILED DESCRIPTION

Embodiments of the invention apply two-photon absorption (TPA) to precisely inject carriers into an IC for the purposes of fault localization using the LADA technique. To generate TPA, embodiments of the invention use a femtosecond pulsed laser with proper energy. The technique is based on two photons arriving simultaneously at a focal point in the transistor, so that the total photon energy is greater than what is needed for electron hole pair creation. Two-photon stimulation requires excitation with femtosecond laser pulses having photon energy less than the bandgap of the semiconductor under test. More specifically, the incident laser photon energy is set to exactly equal or be greater than half the material bandgap. Since two-photon absorption scales quadratically with peak intensity, the signal is strongly localized to the focal spot of the laser, providing an immediate improvement in fault localization and imaging resolution over single photon LADA technique.

Embodiments of the invention also use timing electronics to precisely control the timing of the laser pulse with respect to the transition of an edge of the tester (e.g., ATE) clock. This type of control allows to finely vary the delay or advance of signals propagating through the transistor of interest.

An advantage of the two-photon technique is that it can utilize longer-wavelength light which can be delivered to the transistor with minimal losses. For example, in the case of two photons of 1250 nm light, these will generate the effect of a single photon with a wavelength of 625 nm to create electron hole pairs needed for LADA effect. This in itself will improve the resolution of the current system by almost a factor of 1.21. Furthermore, the non-linear nature of the two-photon generation can be exploited to thereby decrease the volume in which the electron-hole pair generation will occur. In contrast to the single-photon LADA, the carrier generation by two-photon absorption scales nonlinearly with incident power, reducing the effective focal-spot area by 2 and reducing the axial absorption depth from a value comparable to the substrate thickness to only about 100 nm. Thus two-photon stimulation offers a potential reduction in the LADA carrier generation volume of a factor as much as 2000.

Figure 2:
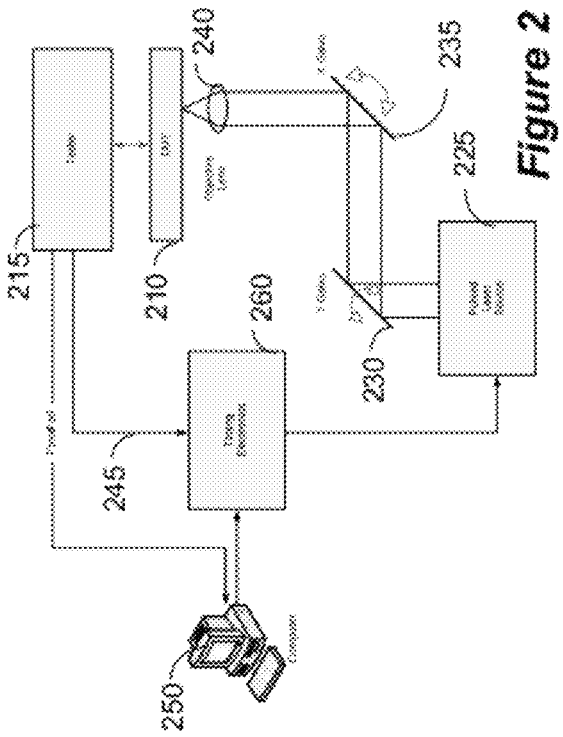
FIG. 2 us a schematic of a system implementing a Two-Photon Laser Assisted Device Alteration technique according to an embodiment of the invention.
Figure 1:
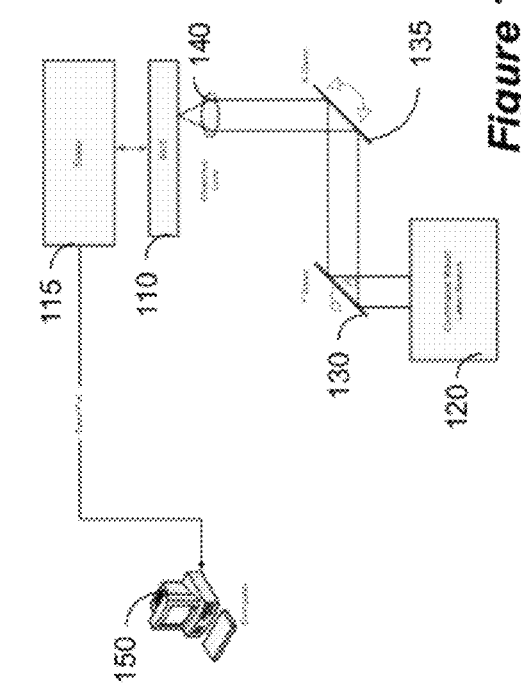
FIG. 1 is a schematic of a LADA system according to the prior art.
Figure 3:
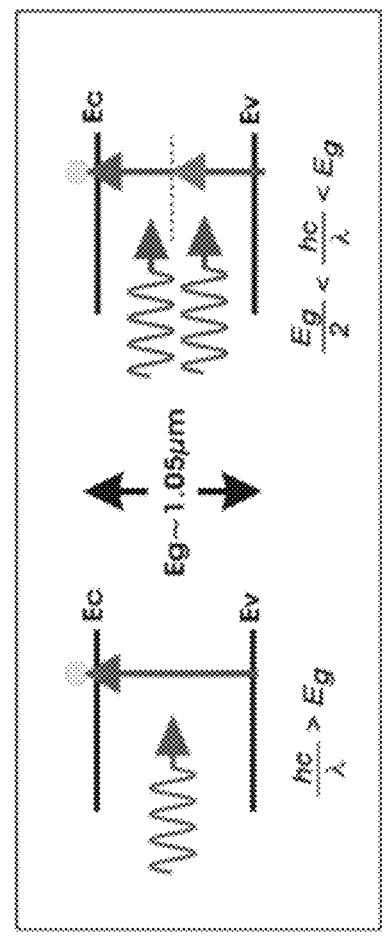
FIG. 3 illustrates a comparison of a single-photon absorption on the left and two-photon absorption on the right.

FIG. 2 illustrates an embodiment of the invention, wherein a DUT 210 is coupled to an ATE 215, as in the prior art. However, in the embodiment of FIG. 2 femtosecond laser pulses are generated by pulsed laser source 225, which are then focused onto the DUT 210 using tiltable mirrors 230 and 235 and objective lens 240. The laser source provides a laser beam of wavelength that is longer than the silicon bandgap, i.e., longer than 1107 nm. In one embodiment wavelength of 1550 nm is used, while in another 1340 nm or 1250 nm are used. In this embodiment, the tiltable mirrors 230 and 235 are implemented as a laser scanning microscope (LSM). Also, in some embodiments a solid immersion lens (SIL) is used as part of the objective lens arrangement.

In conventional LADA systems the laser is always on; however, according to embodiments of the invention very short pulses are used. Therefore, it is important that the device transition occurs when the laser pulse arrives at the device. To achieve that, a trigger signal 245 is obtained from the ATE and input to timing electronics 260, which control the pulsed laser 225 to synchronize the laser pulses with the test signals of the ATE.

Using the system shown in FIG. 2, first the tester (ATE) 215 is operated to apply a set of test vectors to determine the marginal settings of the DUT 210. That is, the voltage and frequency of the test vectors are varied to determine the point where the DUT is just about to fail, or has just failed the test. This is the DUT's pass/fail boundary. The voltage and frequency settings are then used to generate a repetitive test signal to repeatedly stimulate the DUT at its pass/fail boundary.

As the DUT is stimulated at the boundary condition, a sync signal 245 is sent from the tester 215 to the timing electronics 260. The timing electronics 260 controls the laser source 225 to obtain laser pulses of femtosecond pulse width and of wavelength higher than silicon band gap. In general, the wavelength is about 1250 nm to 1550 nm and the pulse width is about 100 fs. The laser pulses are scanned over an area of interest in the DUT 240 to thereby increase or decrease the DUT's switching time and push the DUT beyond the boundary. That is, if the voltage/frequency of the test vector are set such that the DUT is just about to fail, the laser pulses are timed to cause the DUT to fail. Conversely, if the voltage/frequency of the test vector are set such that the DUT is just failing, the laser pulses are timed to cause the DUT to pass the test. During this time the output of the DUT is monitored to determine location of the failure. That is, at the moment in time where the output signal from the DUT indicates a failure (where without the laser beam the DUT would pass), the location of the beam over the DUT is determined, to thereby determine the location of the transistor causing the failure. Conversely, at the moment in time where the output signal from the DUT indicates a pass (where without the laser beam the DUT would fail), the location of the beam over the DUT is determined, to thereby determine the location of the transistor previously causing the failure and now passing.

It should be appreciated that since a sync signal is obtained from the tester, the timing of the laser pulses can be varied so as to vary the amount of the two-photon effect on the transistor. That is, the timing of the laser pulses can be varied so as to increase or decrease the amount of increase or decrease the DUT's switching time. This ability can assist in determining the severity of the fault, in addition to its location.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

The present invention has been described in relation to particular examples, which are intended in all respects to be illustrative rather than restrictive. Those skilled in the art will appreciate that many different combinations of hardware, software, and firmware will be suitable for practicing the present invention. Moreover, other implementations of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A system for performing fault localization in device under test (DUT), wherein the DUT is stimulated by a tester, comprising:
  a laser source providing laser beam pulses of femtosecond pulsewidth and wavelength above silicon bandgap;
  optical elements receiving the laser beam pulses and directing the laser beam pulses onto an area of interest in the DUT;
  timing electronics receiving a sync signal from the tester and controlling the timing of the laser source according to the sync signal wherein the timing electronics control the timing of the laser pulses so as to increase or decrease the DUT switching time;
  wherein the pulsewidth and wavelength of the laser beam pulses are selected so as to cause two-photon absorption in the DUT.

2. The system of claim 1, wherein the laser source provides laser beam pulses of wavelength between 1250 nm to 1550 nm.

3. The system of claim 2, wherein the laser source provides laser beam pulses of about 100 femtosecond pulse width.

4. The system of claim 2, wherein the optical elements comprise a laser scanning microscope (LSM).

5. The system of claim 4, wherein the optical elements further comprise a solid immersion lens.

6. A method for altering the switching time of a device under test, the device being stimulated by test vectors from a tester, comprising:
  generating laser beam pulses of femtosecond pulsewidth and wavelength above silicon bandgap;
  directing the laser beam pulses onto an area of interest in the DUT;
  controlling the timing of the laser source according to sync signal from the tester;
  wherein the pulsewidth and wavelength of the laser beam pulses are selected so as to cause two-photon absorption in the DUT.

7. The method of claim 6, wherein the laser beam pulses are of wavelength between 1250 nm to 1550 nm.

8. The method of claim 6, wherein the laser beam pulses are of about 100 femtosecond pulse width.

9. The method of claim 6, wherein controlling the timing comprises controlling the timing of the laser pulses so as to increase or decrease the DUT switching time.

10. A method for testing a device under test (DUT), the DUT being stimulated by a tester, comprising:
  applying a first set of test vectors from the tester to the DUT to determine the marginal settings of the DUT;
  setting voltage and frequency of a second set of test vectors of the tester according to the marginal settings of the DUT;
  repeatedly applying the second set of test vectors from the tester to the DUT;
  obtaining a sync signal from the tester;
  applying the sync signal to a laser source to obtain laser pulses of femtosecond pulse width and wavelength higher than silicon band gap;
  applying the laser pulses to an area of interest in the DUT to thereby increase or decrease the DUT switching time;
  monitoring the DUT output to determine location of failure.

11. The method of claim 10, wherein monitoring the DUT output comprises at each point in time monitoring a pass-fail of the DUT and correlating the pass-fail result to the location the laser pulses illuminate at that point in time.

12. The method of claim 10, wherein determine the marginal settings comprises determining the voltage and frequency of a test vector such that the DUT is just about to fail the test, or has just failed the test.

* * * * *